United States Patent [19]

Hoffman et al.

[11] 3,963,691

[45] June 15, 1976

[54] SYNTHETIC ANTIGENS OF LUTEINIZING HORMONE RELEASING HORMONE

[75] Inventors: Carl H. Hoffman, Scotch Plains, N.J.; Harvey Schwam, Lafayette Hill; Stephen F. Brady, Meadowbrook, both of Pa.; Martin Hichens, Somerville, N.J.; Ruth F. Nutt, Green Lane, Pa.

[73] Assignee: Merck & Co., Inc., Rahway, N.J.

[22] Filed: Oct. 7, 1974

[21] Appl. No.: 512,563

[52] U.S. Cl............... 260/112.5 LH; 260/112 R; 424/177
[51] Int. Cl.[2]............... C07C 103/52; C07G 7/00
[58] Field of Search......... 260/112.5, 112 R, 112 B; 424/177

[56] References Cited
UNITED STATES PATENTS

| | | | |
|---|---|---|---|
| 3,294,564 | 12/1966 | Karjala et al. | 260/112 B |
| 3,639,558 | 1/1972 | Csizmas et al. | 260/112 B |
| 3,652,761 | 3/1972 | Weetall | 424/177 |
| 3,704,282 | 11/1972 | Spector | 260/112 B |
| 3,709,868 | 1/1973 | Spector | 260/112 B |
| 3,766,162 | 10/1973 | Spector | 260/112 B |
| 3,788,948 | 1/1974 | Kagedal et al. | 260/112 B |
| 3,843,447 | 10/1974 | Burkoth | 260/112 R |
| 3,888,838 | 6/1975 | Immer et al. | 260/112.5 LH |

OTHER PUBLICATIONS

Sievertsson et al.: Biochem. Biophys. Res. Comm., 44, 1566–1571 (1971).

Ben-Efraim et al.: Chem. Abstr. 66:84179p (1967).

Baba et al.: Biochem. Biophys. Res. Comm., 44, 459–463 (1971).

*Primary Examiner*—Lewis Gotts
*Assistant Examiner*—Reginald J. Suyat
*Attorney, Agent, or Firm*—J. Jerome Behan; Walter Patton

[57] ABSTRACT

Synthetic antigens related to luteinizing hormone-releasing hormone (hereinafter designated LH-RH) having the amino acid composition, pyroglutamyl-histidyl-tryptophanylseryl-tyrosyl-glycyl-leucyl-arginyl-prolyl-glycyl-poly-L-lysine (hereinafter designated pyroglu-his-trp-ser-tyr-glyleu-arg-pro-gly-poly-L-lys) and poly-L-lysyl-glutarylhistidyl-tryptophanyl-seryl-tyrosyl-glycyl-leucyl-arginylprolyl-glycine amide (hereinafter designated poly-L-lysglutaryl-his-trp-ser-tyr-gly-leu-arg-pro-gly) are prepared by coupling the corresponding decapeptide with poly-L-lysine. The corresponding decapeptides are prepared by controlled stepwise procedures starting with individual amino acid components. These antigens have the property of inducing formation of antibodies to luteinizing hormone-releasing hormone (LH-RH) in animals.

7 Claims, No Drawings

SYNTHETIC ANTIGENS OF LUTEINIZING HORMONE RELEASING HORMONE

This invention is concerned with the preparation of antigens related to luteinizing hormone-releasing hormone (LH-RH), an important hypothalamic releasing hormone. The antigen is prepared by chemically coupling by a peptide linkage LH-RH related peptides to a suitable carrier. Carriers suitable for this purpose are well known to those skilled in the art. As illustrative examples of naturally occurring protein polymers suitable as carriers are α, β and γ globulins, thyroglobulins and the high molecular weight Keyhole Limpet Hemocyanin. Illustrative examples of synthetic polymers suitable as carriers are polymers prepared from L-amino acids or mixtures of D- and L-amino acids such as poly-L-glutamic acid. An example of a suitable naturally occurring carrier containing sugar is lypopolysaccaride. The preferred carrier for use in the present invention is poly-L-lysine.

LH-RH is a decapeptide having the structure pyroglu-his-trp-ser-tyr-gly-leu-arg-pro-gly-$NH_2$. The peptide, pyroglu-his-trp-ser-tyr-gly-leu-arg-pro-gly, hereinafter referred to as LH-RH-[1-9]-10-glycine-OH, which differs from LH-RH by virtue of the fact that the C-terminal glycine has a free carboxyl, is coupled with a suitable carrier such as poly-L-lysine by reacting the active ester of the peptide, namely the 1-hydroxybenztriazole ester of the C-terminal glycine residue, with poly-L-lysine, thereby substituting some of the free ε-amino groups of the lysyl residues in the poly-L-lysine to form the antigen LH-RH-[1-9]-10-glycyl-poly-L-lysine. In a similar fashion, the LH-RH-related peptide in which the N-terminal pyroglu residue has been replaced by glutaric acid, hereinafter referred to as 1-$N^\alpha$-glutaryl-LH-RH-[2-10], is coupled to poly-L-lysine to form the antigen 1-$N^\alpha$-glutaryl-LH-RH-[1-10]-poly-L-lysine.

These antigens cause the generation of antibodies to LH-RH in animals. Presence of such antibodies controls secretion of LH-RH and other hormones under the control of LH-RH, leading to control of menstrual cycle, ovulation and other important pituitary and gonadal effects. For example, the antigens, LH-RH-[1-9]-10-glycyl-poly-L-lysine and 1-$N^\alpha$-glutaryl-LH-RH-[2-10]-poly-L-lysine, have been used to induce formation of antibodies to LH-RH in animals, for example in rabbits. The antigens of this invention are useful, for example in the veterinary field as an alternative to spaying of canine and feline pets. These synthetic antigens are conveniently administered by injection, thereby effecting the formation of antibodies to follicle stimulating hormone and luteinizing hormone-releasing factor (FSH/LH-RH).

The abbreviated designations, which are used herein for the amino acid components, their derivatives, and certain preferred protecting groups employed in this invention are as follows:

| Amino Acid | Abbreviated Designation |
| --- | --- |
| L-arginine | arg |
| glycine | gly |
| L-histidine | his |
| L-leucine | leu |
| L-proline | pro |
| L-serine | ser |
| L-tryptophane | trp |
| L-tyrosine | tyr |
| L-pyroglutamic acid | pyroglu |

| Derivatives; Protecting Groups | Abbreviated Designation |
| --- | --- |
| N-carboxyanhydride | NCA |
| Nitro | $NO_2$ |
| Tertiary-butyloxycarbonyl | tBOC |
| N-hydroxysuccinimide ester | NHS |
| Methyl ester | OMe |
| Trifluoroacetic acid | TFA |
| Dicyclohexylcarbodiimide | DCC |
| Ethyl ester | OEt |
| N-thiocarboxyanhydride | TCA |

In accordance with the present invention, 1-$N^\alpha$-glutaryl-LH-RH-[2-10] is prepared by stepwise coupling (by peptide linkages) of each of its individual amino acid components, which peptide coupling is conducted by reacting the appropriate amino acid in the sequence (as a derivative in which the carboxyl grouping is activated and any amino groups are protected) first with glycine amide (the amino acid at the C-terminus i.e. carboxy end of the decapeptide chain), and then subsequently with each resulting polypeptide intermediate, such stepwise method being referred to herein as sequential synthesis. When this sequential synthesis is conducted in solution, it is ordinarily preferred to utilize, as the carboxyl activated amino acid, the amino acid NCA, the amino acid TCA, the amino acid azide, or an activated ester such as the NHS ester of such amino acid, or, if desired, to employ a free carboxyl-containing amino acid in conjunction with a coupling agent such as dicyclohexylcarbodiimide. These NCA and TCA sequential synthesis procedures are more fully described in French Pat. No. 1,497,536, granted Sept. 4, 1967.

Alternatively, 1-$N^\alpha$-glutaryl-LH-RH-[2-10] is prepared using solid phase sequential synthesis procedure starting from the C-terminus, also referred to as the Merrifield method. In this procedure, the carboxyl end of the terminal amino acid, glycine (and of the polypeptide product in the following steps), is bound covalently to an insoluble polymeric resin support, as for example as the carboxylic ester of the resin-bonded benzyl alcohol present in hydroxymethyl-substituted polystyrene-divinylbenzene resin. In this solid phase procedure, the peptide coupling may involve direct condensation between the free carboxyl of an amino acid reactant and the amino group of the resin-bonded glycine or polypeptide. Such reaction is ordinarily conducted in the presence of a coupling agent such as dicyclohexylcarbodiimide, although the amino acid reactant may be employed in the form of a carboxy-activated amino acid such as the NHS ester, an amino acid azide, and the like.

Instead of sequential synthesis, 1-$N^\alpha$-glutaryl-LH-RH-[2-10] can also be prepared by block synthesis, wherein various peptide segments of the 1-$N^\alpha$-glutaryl-LH-RH-[2-10] chain are individually synthesized, and these segments are then coupled in proper sequence to form the desired decapeptide product. These peptide segments are themselves conveniently prepared by sequential synthesis in solution using the NCA, TCA, azide or NHS ester procedure or by solid phase sequential synthesis using carboxyl-activated NHS ester or amino acid azide or, if desired, a free carboxyl-containing amino acid reactant in conjunction with a coupling agent such as DCC. The number of amino acid components in the peptide segments used in block synthesis of 1-N$^\alpha$-glutaryl-LH-RH-[2-10] may vary from two to eight, but peptide segments containing five amino acid components or less are preferably utilized, thus avoiding condensations involving larger peptide segments with attendant losses of these more valuable higher peptide fragments.

In carrying out these sequential or block syntheses, involving reaction between carboxyl (or activated carboxyl) of one amino acid and amino grouping of the other, it is ordinarily preferred to protect the amino groupings in the amino acid or peptide undergoing reaction at the carboxyl end of the molecule, as well as other functional groupings in both reactants reactive under the conditions of such syntheses. Protecting groups must retain their protecting properties under the peptide coupling conditions, and must be selectively removable without affecting peptide linkages. Protecting groups to be removed following a particular step must also be selectively removable without affecting other protecting groups to be retained in later coupling steps.

Amino-protecting groups ordinarily employed include salt formation for protecting strongly-basic amino groups, the nitro group being particularly useful for protecting the basic amino group of arginine, acyl-type substituents such as formyl, phthalyl, trifluoroacetyl, toluenesulfonyl, dibenzylphosphoryl, nitrophenylsulfenyl, tritylsulfenyl, o-nitrophenoxyacetyl, and the like, urethane protecting substituents such as benzyloxy-carbonyl (carbobenzoxy), p-methoxycarbobenzoxy, p-nitrocarbobenzoxy, t-butyloxycarbonyl, 2-(p-biphenylyl)-2-propyloxycarbonyl, isonicotinyloxycarbonyl, and the like, alkyl-type substituents such as triphenylmethyl, trialkylsilyl, trimethylsilyl, and the like. It is preferred to utilize tert-butyloxycarbonyl (tBOC) for protecting the α-amino group in the amino acids (or peptides) undergoing reaction at the carboxyl end of the molecule, since the tBOC protecting group is readily removed following such reaction and prior to the subsequent step (wherein such α-amino group itself undergoes reaction) by relatively mild action of acids (e.g. trifluoroacetic acid, or hydrogen chloride in ethyl acetate) which treatment does not affect groupings, such as nitro, carbobenzoxy (Cbz) and isonicotinyloxycarbonyl, used to protect other amino groups such as the basic amino groups of arginine, and removable by vigorous action of a strong acid cleaving agent (e.g. hydrogen bromide in glacial acetic acid or anhydrous hydrogen fluoride in the presence of anisole).

Carboxyl-protecting groups ordinarily employed include amides, salt formation, ester substituents such as the methyl and ethyl esters (which are preferred where subsequent conversion, via the hydrazide, to the azide is desired), the benzyl ester, and particularly the resin-bonded benzyl ester, used in solid phase synthesis (which reacts directly with hydrazine to cleave the peptide from the resin and from the peptide hydrazide), p-nitrobenzylester, t-butyl ester, and the like. Hydroxyl groupings are ordinarily not protected in the synthesis of 1-N$^\alpha$-glutaryl-LH-RH-[2-10] where the coupling reactions are conducted in solution, although tetrahydropyranyl, benzyl trifluoroacetyl, t-butyl, and the like, may be used for such protection if desired. It is usually preferred, however, to use these O-protecting substitutents, and particularly the O-benzyl and O-t-butyl groups, when utilizing solid phase synthesis for the preparation of the serine-containing segment of the 1-N$^\alpha$-glutaryl-LH-RH-[2-10] chain. The imidazole nitrogen of histidine may also be protected, if desired, preferably using an N-hydrocarbon (or substituted-hydrocarbon) substituent such as N-benzyl, N-(2,4-dinitrophenyl), and the like.

The selection of protecting groups is in part dictated by particular coupling conditions, in part by the amino acid and peptide components involved in the reaction.

Guides for selecting particular protecting groups to be employed herein are set forth in detail in the aforesaid French Pat. No. 1,496,536, and the protecting groups disclosed in that patent are incorporated herein by reference.

The preferred overall procedure for preparation of 1-N$^\alpha$-glutaryl-LH-RH-[2-10]-poly-L-lys is outlined diagrammatically in FIG. 1 as follows:

FIG. 1

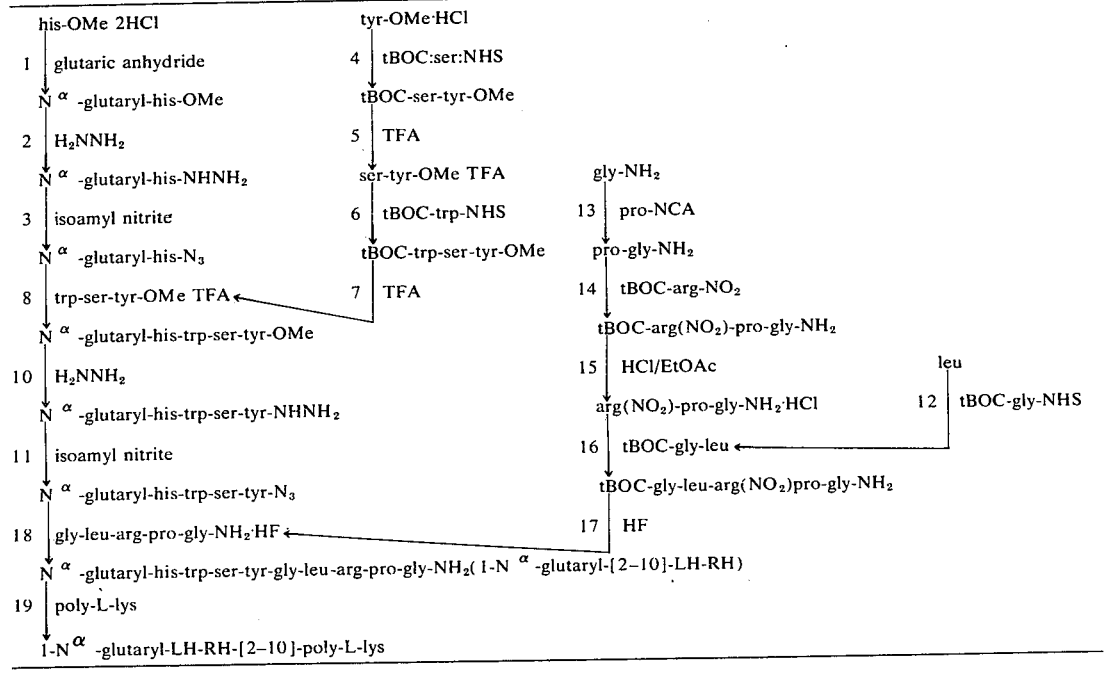

This preferred overall procedure involves combinations of sequential and block synthesis, wherein certain peptide segments of the decapeptide chain are initially formed by the stepwise method, by sequential synthesis in solution, and these segments are then coupled in proper sequence. In this procedure, the tBOC substituent is used to protect α-amino groupings, the $NO_2$ substituent is used to protect the basic primary amino group of arginine, and the methyl ester substituent is used to protect the carboxy groups of histidine, tyrosine, $N^\alpha$-glutaryl-histidine, seryltyrosine, tryptophanyl-seryl-tyrosine and $N^\alpha$-glutaryl-histidyl-tryptophanyl-seryl-tyrosine; in the cases of $N^\alpha$-glutaryl-his and $N^\alpha$-glutaryl-his-trp-ser-tyr, the methyl ester serves the further purpose of providing the intermediates for preparing, via the hydrazide, $N^\alpha$-glutaryl-his azide and $N^\alpha$-glutaryl-his-trp-ser-tyr azide. Instead of this preferred method, however, the present invention also contemplates the various permutations of alternate routes, and employment of other protecting groupings fulfilling criteria hereinabove discussed, such alternate routes likewise involving sequential synthesis in solution, sequential synthesis in solid phase, and combinations of sequential and block synthesis procedures.

As reference to FIG. 1 will show, one preferred overall procedure for preparing 1-$N^\alpha$-glutaryl-LH-RH-[2-10] specifically involves sequential synthesis in solution of (a) the pentapeptide segment, gly-leu-arg-pro-gly-$NH_2$, and (b) the C-terminal carboxyl-activated, pentapeptide segment, $N^\alpha$-glutaryl-his-trp-ser-tyr azide. The former pentapeptide is prepared by reacting gly-$NH_2$ with pro-NCA, which reaction is conducted by vigorously agitating the reactants together in aqueous solution at pH 10.7, under which conditions the reaction is ordinarily complete in about one to two minutes. The alkaline solution is acidified thereby decomposing the intermediate carbamate to form an aqueous solution of pro-gly-$NH_2$, the pH of the solution is then adjusted to pH 9.5, the solution freeze dried, and the residual material extracted with chloroform. Evaporation of the chloroform extract, and crystallization of the residual oil from an organic solvent such as chloroform-ethyl acetate gives substantially pure pro-gly-$NH_2$.

This pro-gly-$NH_2$ is reacted with tBOC-nitroarginine, which reaction is conducted by bringing the reactants together in acetonitrile in the presence dicyclohexylcabodiimide dicyclohexylcarbodiimide at a temperature of about 20°C., under which conditions reaction is ordinarily complete in about 3–4 hours. The reaction mixture is evaporated in vacuo, the residual oil is dissolved in water, and the aqueous solution extracted with a water-immiscible solvent such as chloroform; the aqueous solution is then evaporated in vacuo, and the residual material purified by chromatography to give substantially pure tBOC-arg($NO_2$)-pro-gly-$NH_2$. This tripeptide is treated with hydrogen chloride in ethyl acetate, thereby cleaving the tBOC substituent to form arg($NO_2$)-pro-gly-$NH_2$ hydrochloride.

The dipeptide segment tBOC-gly-leu is prepared by reacting leucine with the NHS ester of tBOC-glycine in ethanol solution under alkaline conditions (preferably pH 8.0), thereby forming tBOC-gly-leu; this protected dipeptide is then reacted with arg($NO_2$)-pro-gly-$NH_2$ by bringing the reactants together in dimethyl formamide, adjusting the pH to 9.5 by addition of triethylamine, and then adding a solution of hydroxybenztriazole in methylene chloride, followed by a solution of dicyclohexylcarbodiimide in methylene chloride. Under these conditions, the tBOC-gly-leu reacts initially with the hydroxybenztriazole to form the corresponding active ester [which protects the dipeptide from racemization during reaction with the arg($NO_2$)-pro-gly-$NH_2$]. The reaction mixture is stirred at about 25°C. for a period of about 3–4 hours, at the end of which time the reaction of the said hydroxybenztriazole ester of tBOC-gly-leu with the arg($NO_2$)-pro-gly-$NH_2$ to form the pentapeptide is substantially complete. The reaction mixture is evaporated in vacuo, the residual material is triturated with an organic solvent such as ethyl acetate, and purified by chromatography to give substantially pure tBOC-gly-leu-arg($NO_2$)-pro-gly-$NH_2$. This protected pentapeptide is then reacted with anhydrous hydrogen fluoride, preferably in the presence of anisole at a temperature of below about 0°C., under which conditions cleavage of both the tBOC and nitro substituents is complete in about 30 minutes. Excess hydrogen fluoride is conveniently removed by passing a stream of nitrogen through the reaction mixture. The latter is then triturated with ether, dissolved in acetic acid, and the acetic acid solution evaporated in the cold, preferably by freeze-drying to give the unprotected pentapeptide-amide salt, gly-leu-arg-pro-gly-$NH_2$ hydrofluoride.

The terminal tripeptide sequence of the N-terminal pentapeptide, in the form of its alkyl ester trifluoroacetate, such as trp-ser-tyr-OMe TFA, trp-ser-tyr-OEt TFA, and the like, is prepared by first reacting the tyrosine alkyl ester with the NHS ester of tBOC-serine in dimethylformamide solution under alkaline conditions (preferably pH 8.0), thereby forming tBOC-ser-tyr-OMe or tBOC-ser-tyr-OEt; this dipeptide is treated with trifluoroacetic acid thereby forming ser-tyr-OMe trifluoroacetate or ser-tyr-OEt trifluoro acetate. This ser-tyr alkyl ester TFA is reacted with NHS ester of tBOC-trp in dimethylformamide solution under mildly alkaline conditions (preferably pH 8.0) to form the tripeptide, tBOC-trp-ser-tyr-OMe or tBOC-trp-ser-tyr-OEt, which is reacted with trifluoroacetic acid thereby forming trp-ser-tyr-OMe TFA or trp-ser-tyr-OEt TFA.

The remaining segment of this N-terminal pentapeptide, in the form of its azide, namely $N^\alpha$-glutaryl-his-$N_3$, is prepared by first reacting the methyl ester of histidine dihydrochloride with glutaric anhydride in dimethylformamide containing triethylamine, preferably at pH 8.0. The mixture is stirred at a temperature of about 25°C., under which conditions the reaction is complete in about 20–25 hours. The reaction mixture is evaporated in vacuo and the residual oil is triturated with chloroform to afford a solid, which is isolated by filtration and reacted with hydrazine. The resulting hydrazide is treated with isoamyl nitrite thereby forming $N^\alpha$-glutaryl-his azide.

This $N^\alpha$-glutaryl-his azide is then reacted with the alkyl ester of trp-ser-tyr in dimethylformamide solution under mildly alkaline conditions (preferably pH 8.0) to form the corresponding pentapeptide, $N^\alpha$-glutaryl-his-trp-ser-tyr-OMe or $N^\alpha$-glutaryl-his-trp-ser-tyr-OEt, which is, in turn, reacted with hydrazine, and the resulting hydrazine treated with isoamyl nitrite, thereby forming $N^\alpha$-glutaryl-his-trp-ser-tyr azide.

The two pentapeptides gly-leu-arg-pro-gly-$NH_2$ and $N^\alpha$-glutaryl-his-trp-ser-tyr azide are reacted in dimethylformamide solution under mildly alkaline conditions (preferably pH 8.0), thereby forming the decapeptide, $N^\alpha$-glutaryl-his-trp-ser-tyr-gly-leu-arg-progly-NH$_2$, herein also referred to as 1-N$^\alpha$-glutaryl-LH-RH-[2-10].

The free carboxyl of the N-terminal glutaryl residue is converted to the 1-hydroxybenztriazole "active ester" by the action of DCC. The "active ester" is coupled to poly-L-lysine thereby producing the antigen 1-N$^\alpha$-glutaryl-LH-RH-[2-10]-poly-L-lys.

The preferred overall procedure for preparation of LH-RH-[1-9]-10-glycyl- poly-L-lysine is outlined diagrammatically in FIG. 2 as follows:

glycine is reacted with the carboxyl group of tBOC-pro in the presence of DCC to form tBOC-pro-gly-resin. This series of steps is repeated with the exception that the tBOC-amino acid next in the desired sequence is attached to the pro-gly-resin. In this manner the amino acids proline, nitroarginine, leucine and glycine are sequentially attached to the gly-resin. After the desired amino acid sequence has been obtained, the peptide-resin is treated with liquid hydrogen fluoride preferably at 0°C., under which conditions the cleavage of the

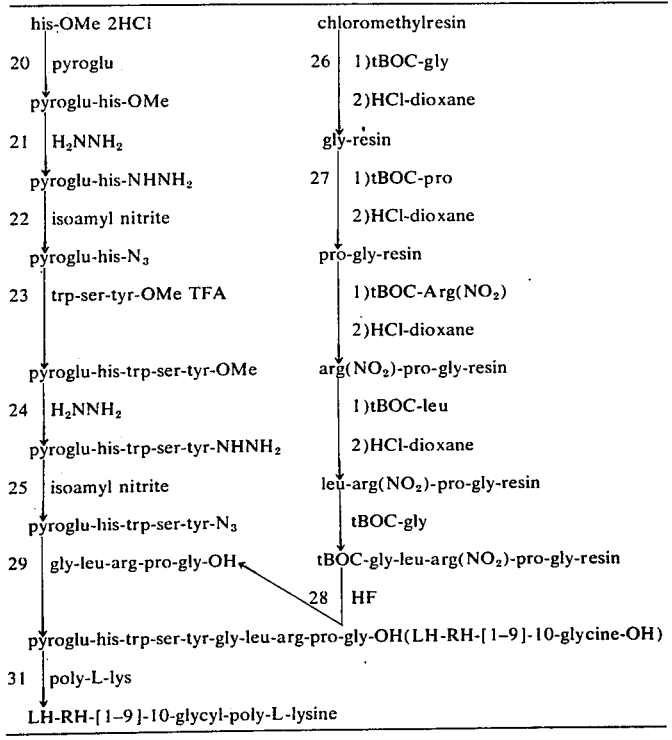

The number appearing next to each arrow refers to the illustrative example which sets forth the experimental details for the indicated conversion.

As reference to FIG. 2 will show, the preferred overall procedure for preparing LH-RH-[1-9]-10-glycyl-poly-L-lysine specifically involves sequential synthesis using the solid phase Merrifield method of (a) the pentapeptide segment, gly-leu-arg-pro-gly-OH, and sequential synthesis in solution of (b) the carboxyl-activated, pentapeptide segment, pyroglu-his-trp-ser-tyr azide. The former pentapeptide is prepared by reacting tBOC-gly with chloromethylated resin, which reaction is carried out in peroxide-free tetrahydrofuran at a temperature of about 76°C. The reaction is ordinarily complete in 45 minutes. The tBOC-gly-resin is stirred with triethylamine at about 76°C. for about 77 hours, after which it is transferred into a Merrifield solid phase rocking reaction vessel. The tBOC-gly-resin is carried through a series of steps wherein the tBOC group is removed and the resulting amine group of the peptide from the resin and removal of both the tBOC and nitro protecting groups is completed in about 30 minutes. The product is extracted into acetic acid and freeze-dried to give the unprotected gly-leu-arg-pro-gly-OH hydrofluoride.

The terminal tripeptide sequence of the N-terminal pentapeptide, in the form of its alkyl ester trifluoroacetate, such as trp-ser-tyr-OMe TFA, trp-ser-tyr-OEt TFA, and the like, is prepared by the method described in Examples 4, 5, 6 and 7.

The remaining dipeptide segment of the N-terminal pentapeptide, in the form of its azide, namely pyroglu-his-N$_3$, is prepared by first reacting the methyl ester of histidine with pyroglutamic acid in acetonitrile containing triethylamine, in the presence of dicyclohexylcarbodiimide. The mixture is stirred at a temperature of about 25°C., under which conditions the reaction is complete in about 20–25 hours. The reaction mixture is evaporated in vacuo to a small volume, and the resulting mixture is filtered, thereby separating dicyclohexulurea. The filtrate is diluted with several volumes of ether, and the material which precipitates is recovered by filtration, and crystallized from an organic solvent such as isopropanol to give pyroglu-his-OMe. The latter is reacted with hydrazine, and the resulting hydrazide is treated with isoamyl nitrite thereby forming pyroglu-his azide.

This pyroglu-his azide is then reacted with the alkyl ester of trp-ser-tyr (prepared by the method described in Examples 4, 5, 6 and 7) in dimethylformamide solution under mildly alkaline conditions (preferably pH 8.0) to form the corresponding pentapeptide, pyroglu-his-trp-ser-tyr-OMe or pyroglu-his-trp-ser-tyr-OEt, which is, in turn, reacted with hydrazine, and the resulting hydrazine treated with isoamyl nitrite, thereby forming pyroglu-his-trp-ser-tyr azide.

The two pentapeptides gly-leu-arg-pro-gly-OH and pyroglu-his-trp-ser-tyr azide are reacted in dimethylformamide solution under mildly alkaline conditions (preferably pH 8.0), thereby forming the decapeptide, pyroglu-his-trp-ser-tyr-gly-leu-arg-pro-gly-OH, herein also referred to as LH-RH-[1-9]-10-glycine-OH.

After the decapeptide has been purified by passing through a Sephadex G-25 molecular sieve and a silica gel dry column the free carboxyl on the C-terminal glycine residue is converted to a 1-hydroxybenztriazole "active ester" by the action of DCC. The "active ester" is coupled with poly-L-lysine thereby producing the antigen LH-RH-[1-9]-10-glycyl-poly-L-lysine.

In accordance with the present invention, poly-L-lysine is prepared by treating $N^\epsilon$-protected-L-lysine-N-carboxyanhydride with a base. The alkaline solution is acidified thereby decomposing the intermediate carbamate to form a solution of $N^\epsilon$-protected-poly-L-lysine. The solvent is removed under vacuum and the residue dissolved in veratrole and treated with hydrogen fluoride to remove the $N^\epsilon$-protecting groups. The hydrogen fluoride is removed with a stream of nitrogen and the residue triturated with ether. The residue is dissolved in pH 6 buffer and washed with chloroform. The supernatant is passed through a Sephadex column to obtain material having an average molecular weight in the range of 40,000–80,000. This material is further treated by passing through an ion exchange column to obtain the hydrochloride salt of poly-L-lysine.

Synthetic amino acid polymers suitable as carriers are prepared by the method described above wherein $N^\epsilon$-protected-L-lysine-N-carboxyanhydride is substituted by other suitably protected D- or L-amino acids.

The antigens of this invention are iodinated with $^{125}I$ and may be used in the radioimmuno assay of LH-RF.

The following examples illustrate methods of carrying out the present invention, but it is to be understood that these examples are given for purposes of illustration and not of limitation.

EXAMPLE 1

Preparation of $N^\alpha$-Glutaryl-His-OMe

A solution of 428 mg. of his-OMe dihydrochloride, 274 mg. of glutaric anhydride and 1.6 ml. of triethylamine (3 equivalents) in 10 ml. of dry dimethylformamide, is maintained at a pH of 8. The resulting mixture is stirred for a period of 20 hours while maintaining the temperature at 25°C., and the reaction mixture is evaporated in vacuo. The resulting mixture is triturated with several portions of chloroform to give a tacky solid which is suitable for use in the next step.

EXAMPLE 2

Preparation of $N^\alpha$-Glutaryl-His Hydrazide

To 0.5 g. of $N^\alpha$-glutaryl-his-OMe dissolved in 4 ml. of methanol is added 4 ml. of anhydrous hydrazine. The resulting mixture is stirred for 6 minutes at room temperature, and the reaction mixture is then evaporated in vacuo at a temperature of 35°C. Ten ml. of ethanol is added to the residual material, and the resulting mixture is evaporated in vacuo; 10 ml. of dimethylformamide is then added and the resulting mixture is evaporated in vacuo. The residual solid is triturated with dimethylformamide and after filtration ethanol is added to induce crystallization. Thus, 0.23 g. of $N^\alpha$-glutaryl-his hydrazide is obtained. Recrystallization from hot methanol gives 0.17 g. of the hydrazide.

EXAMPLE 3

Preparation of $N^\alpha$-Glutaryl-His Azide

A suspension of 0.11 g. of $N^\alpha$-glutaryl-his hydrazide, prepared as described in Example 2, in 14 ml. of freshly degassed dimethylformamide, is cooled to a temperature of −40°C. and maintained under a dry nitrogen atmosphere to exclude moisture. To the cold suspension is added, with stirring, a solution of 1.4 ml. of 2N hydrogen chloride in tetrahydrofuran followed by 0.5 ml. of a 10% v/v solution of isoamylnitrite in dimethylformamide. The resulting mixture is maintained under a dry nitrogen atmosphere at a temperature of −15°C. to −20°C. for a period of 2.5 hours, at the end of which time the hydrazide has completely reacted to form $N^\alpha$-glutaryl-his azide.

EXAMPLE 4

Preparation of tBOC-Ser-Tyr-OMe

The pH of a solution of 2.54 g. of tyr-OMe hydrochloride and 3.02 g. of the NHS ester of tBOC-ser in 100 ml. of freshly degassed dimethylformamide is adjusted to pH 8.0 by the addition of diisopropylethylamine, and stirred for a period of about four hours, while maintaining the temperature at 25°C. and the pH at 8.0 by the addition of diisopropylethylamine. The reaction mixture is evaporated in vacuo, the residual oil is dissolved in methylene chloride, and the methylene chloride solution is washed twice with 0.2N aqueous sulfuric acid solution saturated with sodium sulfate, once with saturated aqueous sodium chloride solution, twice with saturated aqueous sodium bicarbonate solution, and finally twice with saturated aqueous sodium chloride solution. The washed methylene chloride solution is then dried over anhydrous sodium sulfate, evaporated in vacuo, and the residual oil is crystallized from ethyl acetate-hexane to give 3.2 g. of crystalline tBOC-ser-tyr-OMe.

EXAMPLE 5

Preparation of Ser-Tyr-OMe Trifluoroacetate

A sample of 3.0 g. of tBOC-ser-tyr-OMe, prepared as described in Example 4, is dissolved (at a temperature of 0°C.) in the minimum quantity of trifluoroacetic acid, and the solution is stirred at a temperature of 25°C. for a period of 45 minutes. The solution is then added dropwise with vigorous stirring to 100 ml. of ether. The material which precipitates is recovered by filtration, washed with ether, and dried in vacuo to give 3.0 g. of ser-tyr-OMe trifluoroacetate.

EXAMPLE 6

Preparation of tBOC-Trp-Ser-Tyr-OMe

A solution of 2.83 g. of ser-tyr-OMe trifluoroacetate, prepared by the method described in Example 5, and 2.48 g. of the NHS ester of tBOC-trp is prepared in 60 ml. of freshly degassed dimethylformamide. The resulting solution is adjusted to pH 8.0 by the addition of triethylamine, and stirred for a period of 1.5 hours while maintaining the temperature at 25°C. and the pH at 8.0 by the addition of triethylamine. The reaction mixture is filtered and evaporated in vacuo. The residual syrup is dissolved in 100 ml. chloroform, and the solution is washed with 0.2N aqueous sulfuric acid solution, then with saturated aqueous sodium bicarbonate solution, and finally with water. The washed chloroform solution is dried over anhydrous sodium sulfate, partially evaporated in vacuo, and the product which crystallizes is recovered by filtration and dried to give 2.4 g. of crystalline tBOC-trp-ser-tyr-OMe.

EXAMPLE 7

Preparation of Trp-Ser-Tyr-OMe Trifluoroacetate

A suspension of 1.2 g. of tBOC-trp-ser-tyr-OMe, prepared in Example 6, is prepared in 4.3 ml. of dimethylsulfide, and the mixture dissolved (at a temperature of 0°C.) in 13 ml. of trifluoroacetic acid. The resulting solution is stirred at a temperature of 25°C. for a period of 12 minutes, and the solution is then added dropwise, with vigorous stirring, to 250 ml. of ether. The material which precipitates is recovered by filtration, washed twice with ether, and dried in vacuo to give 1.1 g. of trp-ser-tyr-OMe trifluoroacetate.

EXAMPLE 8

Preparation of $N^\alpha$-Glutaryl-His-Trp-Ser-Tyr-OMe

The reaction solution containing $N^\alpha$-glutaryl-his azide, prepared as described in Example 3, is cooled to a temperature of −40°C., and to this is added a solution of 0.24 g. of trp-ser-tyr-OMe trifluoroacetate in 2 ml. of degassed dimethylformamide. The pH of the resulting solution is adjusted to 8.0 by the addition of diisopropylethylamine, and the mixture is maintained at a temperature of −5°C. (with periodic adjustment of the pH to 8.0 by addition to diisopropylethylamine) for a period of 70 hours, at the end of which time the reaction to form the pentapeptide is substantially complete as may be shown by thin layer chromatography on silica gel G using the solvent system ethyl acetate-pyridine-acetic acid-water (10:5:1:3). The reaction solution is evaporated in vacuo; the residual material is dissolved in 50 ml. butanol; the butanol solution is washed with three 25 ml.-portions of water; the combined water washings are extracted with six 10 ml.-portions of butanol; and the combined butanol solutions are evaporated to a small volume. The crystalline material which precipitates after addition of chloroform is recovered by filtration, dried and further purified by dissolution in water and adjustment of the pH to 5.1 (the calculated iso-electric point), whereupon precipitation occurs to give 0.13 g. of $N^\alpha$-glutaryl-his-trp-ser-tyr-OMe.

EXAMPLE 9

Preparation of $N^\alpha$-Glutaryl-His-Trp-Ser-Tyr-OEt

In accordance with the procedures set forth in Examples 4-8 hereinabove, but utilizing tyr-OEt hydrochloride as starting material in place of the tyr-OMe hydrochloride employed in Example 4, there are obtained, respectively, tBOC-ser-tyr-OEt; ser-tyr-OEt TFA; tBOC-trp-ser-tyr-OEt; trp-ser-tyr-OEt TFA; and $N^\alpha$-glutaryl-his-trp-ser-tyr-OEt.

EXAMPLE 10

Preparation of $N^\alpha$-Glutaryl-His-Trp-Ser-Tyr Hydrazide

To 0.11 g. of either $N^\alpha$-glutaryl-his-trp-ser-tyr-OMe, prepared as described in Example 8, or $N^\alpha$-glutaryl-his-trp-ser-tyr-OEt, is added 6 ml. of 1:1 mixture of anhydrous hydrazine and methanol. The resulting mixture is stirred for 6 minutes at room temperature, and the reaction mixture is evaporated in vacuo at a temperature of 35°C. Ten ml. of ethanol is added to the residual material, and the resulting mixture is evaporated in vacuo; 10 ml. of dimethylformamide is then added and the resulting mixture is evaporated in vacuo. The residue is triturated with isopropanol, and the resulting solid dried in vacuo to give 0.10 g. of $N^\alpha$-glutaryl-his-trp-ser-tyr-hydrazide.

EXAMPLE 11

Preparation of $N^\alpha$-Glutaryl-His-Trp-Ser-Tyr Azide

A suspension of 96 mg. of $N^\alpha$-glutaryl-his-trp-ser-tyr-hydrazide, prepared as described in Example 10, is made in 20 ml. of freshly degassed dimethylformamide. The suspension is cooled to a temperature of −40°C. and maintained under a dry nitrogen atmosphere to exclude moisture. To the cold suspension is added, with stirring, a solution of 0.7 ml. of 2N hydrogen chloride in tetrahydrofuran, followed by 0.17 ml. of a 10% v/v solution of isoamylnitrite in dimethylformamide. The resulting mixture is maintained under a dry nitrogen atmosphere at a temperature of −15°C. to −20°C. for a period of 3.5 hours, at the end of which time the hydrazide is completely reacted to form $N^\alpha$-glutaryl-his-trp-ser-tyr azide.

EXAMPLE 12

Preparation of tBOC-Gly-Leu

To an aqueous solution of 4.58 g. of leu is added 200 ml. of ethanol, and the pH is adjusted to 8.0 by the addition of 50% aqueous potassium hydroxide solution. About 9.54 g. of the NHS ester of tBOC-gly is added with stirring to this leu solution, while maintaining the temperature at about 25°C. and the pH at 8.0 by the dropwise addition of 50% aqueous sodium hydroxide solution. When base consumption ceases, the reaction solution is filtered, the ethanol is evaporated therefrom in vacuo, and the aqueous reaction solution is extracted with 300 ml. of ethyl acetate, thereby extracting unreacted NHS ester present in said solution. The pH of the aqueous reaction solution is then adjusted to 2.5 by the addition of concentrated sulfuric acid, and the acidified solution is extracted with three 300 ml.-portions of ethyl acetate; these latter ethyl acetate extracts are combined, dried over anhydrous sodium sulfate, and the ethyl acetate evaporated therefrom in vacuo. Thin layer chromatography of the residual material on silica gel, using chloroform-methanol-water (80:18;2) as eluant, shows this product to be substantially pure tBOC-gly-leu.

EXAMPLE 13

Preparation of Pro-Gly-$NH_2$

A solution is prepared by dissolving 2.2 g. of gly-$NH_2$ in 200 ml. of 1M aqueous potassium borate buffer (pH=10.7). This buffer is conveniently prepared as follows: one mole of boric acid is slurried in 500 ml. of water, and solid potassium hydroxide merely sufficient to dissolve the boric acid is added; additional potassium hydroxide is then added to bring the pH to 10.7, the solution is diluted to 990 ml., the pH is again adjusted to 10.7, and the solution diluted to a final volume of 1000 ml. The solution containing the gly-$NH_2$ is cooled to 0°C., and 3.52 g. of pro-NCA is added to the solution in a single charge, during which time the mixture is vigorously agitated (preferably using a Waring blender) while maintaining the temperature at 0°C. and the pH at 10.7 by the dropwise addition of 50% aqueous potassium hydroxide. The reaction is allowed to proceed, while continuing agitation and maintaining temperature at 0°C. and pH at 10.7, until base consumption ceases (about 1 minute); sufficient concentrated sulfuric acid is added to bring the pH to 2.5; and nitrogen is bubbled through the acidified reaction mixture for about 30 minutes, thereby sweeping carbon dioxide from the resulting solution of pro-gly-$NH_2$. The pH of this solution is adjusted to 9.5 with 50% potassium hydroxide solution, the solution is then freeze-dried, and the residual material is extracted with chloroform. The chloroform extract is filtered, evaporated to dryness, and the resulting oil is crystallized from chloroform-ethyl acetate to give 3.2 g. of substantially pure pro-gly-$NH_2$.

EXAMPLE 14

Preparation of tBOC-Arg($NO_2$)-Pro-Gly-$NH_2$

To a solution of 170 mg. of pro-gly-$NH_2$ and 320 mg. of tBOC-nitroarginine in 10 ml. of acetonitrile is added 227 mg. of dicyclohexylcarbodiimide with stirring, and the mixture is stirred at a temperature of 20°C. for 3.5 hours. The reaction mixture is evaporated in vacuo, the residual oil is dissolved in water, and the aqueous solution is extracted with two 50 ml.-portions of chloroform. The aqueous solution is then evaporated in vacuo, and the residual oil is purified by chromatography on silica gel using chloroform-methanol-water (50:40:10) as eluant to give 80 mg. of pure tBOC-arg($NO_2$)-pro-gly-$NH_2$.

EXAMPLE 15

Preparation of Arg($NO_2$)-Pro-Gly-$NH_2$ Hydrochloride

A suspension of 1.1 g. of the tBOC-arg($NO_2$)-pro-gly-$NH_2$ in 100 ml. of ethyl acetate is prepared. The temperature is adjusted to 5°C., and anhydrous hydrogen chloride gas is bubbled into the mixture (maintained at 5°C.) for 7 minutes. A stream of nitrogen is then passed through the reaction mixture until the latter is substantially purged of hydrogen chloride. The precipitated material is recovered by filtration, washed with ethyl acetate and dried in vacuo at 25°C. to give 1.1 g. of substantially pure arg($NO_2$)-pro-gly-$NH_2$ hydrochloride.

EXAMPLE 16

Preparation of tBOC-Gly-Leu-Arg($NO_2$)-Pro-Gly-$NH_2$

A solution of 890 mg. of arg($NO_2$)-pro-gly-$NH_2$ hydrochloride and 567 mg. of tBOC-gly-leu is prepared in 10 ml. of freshly degassed dimethylformamide. The resulting solution is adjusted to pH 9.5 by the addition of triethylamine. A solution of 440 mg. of hydroxybenztriazole in 18 ml. of methylene chloride is added, followed by a solution of 540 mg. of dicyclohexylcarbodiimide in 12 ml. of methylene chloride, and the mixture is stirred for a period of 3.5 hours while maintaining the temperature at 25°C. The reaction mixture is evaporated in vacuo, and triturated with ethyl acetate. The resulting solid (1.2 g.) is subjected to chromatography on silica gel using a mixture of chloroform: methanol:water (80:18:2) as eluant to give 300 mg. of substantially pure tBOC-gly-leu-arg($NO_2$)-pro-gly-$NH_2$.

EXAMPLE 17

Preparation of Gly-Leu-Arg-Pro-Gly-$NH_2$ Hydrofluoride

A 200 mg. portion of tBOC-gly-leu-arg($NO_2$)-pro-gly-$NH_2$ is dried in vacuo over phosphorus pentoxide for a period of 15 hours, thereby removing traces of water, and the resulting dry material is placed in a polyethylene tube containing 0.3 ml. of anisole. The mixture is cooled to −78°C.. Four ml. of anhydrous hydrogen fluoride is condensed in the tube, and the resulting mixture is stirred at a temperature of 0°C. for 30 minutes. At the end of this reaction period, a stream of dry nitrogen is passed through the mixture (still at 0°C.), thereby removing excess hydrogen fluoride. The residual material is held in vacuo at a temperature of 25°C. for 20 minutes, triturated with ether, washed with ether, dissolved in aqueous acetic acid, and the aqueous acetic acid solution is freeze-dried to give 190 mg. of substantially pure gly-leu-arg-pro-gly-$NH_2$ hydrofluoride.

EXAMPLE 18

Preparation of $N^\alpha$-Glutaryl-His-Trp-Ser-Tyr-Gly-Leu-Arg-Pro-Gly-$NH_2$ The reaction solution containing $N^\alpha$-glutaryl-his-trp-ser-tyr azide, prepared as described in Example 11, is cooled to a temperature of −40°C., and to this is added a solution of 76 mg. of gly-leu-arg-pro-gly-$NH_2$ hydrofluoride in 2 ml. of degassed dimethylformamide. The pH of the resulting solution is adjusted to 8 by the addition of diisopropylethylamine, and the mixture is maintained at −5°C. (with periodic adjustment of the pH to 8.0 by addition of diisopropylethylamine) for a period of 18 hours, at the end of which time the reaction to form the decapeptide is substantially complete as may be shown by thin layer chromatography on silica gel G using the solvent system ethyl acetate-pyridine-acetic acid-water (5:5:1:3). The reaction solution is evaporated in vacuo; the residual material is triturated with ethanol; and the resulting solid material is washed three times with ethanol, suspended in water and lyophilized to give 68 mg. of substantially pure $N^\alpha$-glutaryl-his-trp-ser-tyr-gly-leu-arg-pro-gly-$NH_2$ also designated 1-$N^\alpha$-glutaryl-LH-RH-[2-10].

EXAMPLE 19

Preparation of 1-N$^\alpha$-glutaryl-LH-RH-[2-10] Coupled to Poly-L-Lysine

To a solution of 0.021 mmoles (25 mg.) of 1-N$^\alpha$-glutaryl-LH-RH-[2-10] (glutaryl-His-Trp-Ser-Tyr-Gly-Leu-Arg-Pro-Gly-NH$_2$) and 0.075 mmoles (1.05 mg.) 1-hydroxybenztriazole in 0.25 ml. freshly distilled DMF is added 0.42 mmoles of dicyclohexylcarbodiimide (DCC) in 0.175 ml. of CH$_2$Cl$_2$. The solution is kept at 4°C. for 17 hours, taken to dryness with a stream of dry N$_2$ and extracted two times with 1 ml. each of CH$_2$Cl$_2$ to remove unreacted DCC.

The active ester of 1-N$^\alpha$-glutaryl-LH-RH-[2-10] is dissolved in 0.25 ml. of DMF and added to a solution of 50 mg. poly-L-lysine (Mol. Wt. average 40,000) in 0.5 ml. DMF, 0.25 ml. water made pH 9.7 with triethylamine. After the mixture is stirred for 72 hours at room temperature, it is dialysed against water and lyophylized to yield 55 mg. of product which is free of unbound LH-RH analog when examined by thin-layer chromatography (silicic acid plates; solvent system; chloroform:methanol:ammonium hydroxide, 60:40:10; while the unbound LH-RH analog moves, the 1-N$^\alpha$-glutaryl-LH-RH-[2-10] remains at the origin). The amino acid analysis is as follows: Lys, 1.42; His, 0.096; Arg, 0.102; Ser, 0.094; Pro, 0.098; Gly, 0.202; Leu, 0.101; Tyr, 0.100; Trp, 0.088. On the basis of the amino acid analysis the ratio of 1-N$^\alpha$-glutaryl-LH-RH-[2-10] to poly-L-lysine is 14:1. The product is chromatographed in 50:40:10 (chloroform:methanol:water) and when sprayed with t-butylhypochlorite-KI starch and Ehrlich's reagent shows only a single spot.

EXAMPLE 20

Preparation of Pyroglu-his-OMe

To a solution of 12.1 g. of his-OMe hydrochloride, 6.5 g. of pyroglutamic acid and 14 ml. of triethylamine in 200 ml. of acetonitrile is added, with stirring, 12.8 g. of dicyclohexylcarbodiimide. The resulting mixture is stirred for a period of 22 hours while maintaining the temperature at 25°C., and the reaction mixture is evaporated in vacuo to a volume of 50 ml. The resulting mixture is filtered, thereby separating precipitated dicyclohexylurea, and the latter is washed with acetonitrile and then with methanol. The combined filtrates are evaporated in vacuo to a volume of 50 ml.. Two hundred ml. of ether is added to the concentrated solution, and the material which precipitates is recovered by filtration, and crystallized from isopropanol to give 5.0 g. of crystalline pyroglu-his-OMe.

EXAMPLE 21

Preparation of Pyroglu-his Hydrazide

To 0.2 g. of pyroglu-his-OMe is added 10 ml. of a 1:1 mixture of anhydrous hydrazine and methanol. The resulting mixture is stirred for 6 minutes at room temperature, and the reaction mixture is then evaporated in vacuo at a temperature of 35°C. Ten ml. of ethanol is added to the residual material, and the resulting mixture is evaporated in vacuo; 10 ml. of dimethylformamide is then added and the resulting mixture is evaporated in vacuo. The residual oil is triturated with ethanol, dried in vacuo at room temperature, and crystallized from methanol to give 0.19 g. of pyroglu-his hydrazide.

EXAMPLE 22

Preparation of Pyroglu-his Azide

A suspension of 0.63 g. of pyroglu-his hydrazide, prepared as described in Example 21, in 80 ml. of freshly degassed dimethylformamide is cooled to a temperature of −40°C. and maintained under a dry nitrogen atmosphere to exclude moisture. To the cold suspension is added, with stirring, a solution of 4.0 ml. of 3N hydrogen chloride in tetrahydrofuran followed by 0.3 ml. of isoamylnitrite. The resulting mixture is maintained under a dry nitrogen atmosphere at a temperature of −15°C. to −20°C. for a period of about 2.5 hours, at the end of which time the hydrazide is completely reacted to form pyroglu-his azide.

EXAMPLE 23

Preparation of Pyroglu-His-Trp-Ser-Tyr-OMe

The reaction solution containing pyroglu-his azide, prepared as described in Example 22, is cooled to a temperature of −40°C., and to this is added a solution of 1.1 g. of trp-ser-tyr-OMe trifluoroacetate, as prepared in Example 4, 5, 6 and 7, in 4 ml. of degassed dimethylformamide. The pH of the resulting solution is adjusted to 8.0 by the addition of diisopropylethylamine, and the mixture is maintained at a temperature of −5°C. (with periodic adjustment of the pH to 8.0 by addition of diisopropylethylamine) for a period of 18 hours, at the end of which time the reaction to form the pentapeptide is substantially complete as shown by thin layer chromatography on silica gel G using the solvent system ethyl acetate-pyridine-acetic acid-water (10:5:1:3). The reaction solution is evaporated in vacuo; the residual material is dissolved in 50 ml. butanol; the butanol solution is washed with three 25 ml.-portions of water; the combined water washings are extracted with six 10 ml.-portions of butanol; and the combined butanol solutions are evaporated to a small volume. The crystalline material which precipitates is recovered by filtration, dried and further purified by chromatography on a silica gel column to give 0.5 g. of substantially pure pyroglu-his-trp-ser-tyr-OMe.

EXAMPLE 24

Preparation of Pyroglu-His-Trp-Ser-Tyr-NHNH$_2$

A solution of 290 mg. of pyroglu-his-trp-ser-tyr-OMe in 8 ml. of methanol is cooled to 0°C. and flushed with nitrogen and treated, while stirring, with 7 ml. of hydrazine. After the solution is stirred for an additional 10 minutes at 20°C., the solvents are evaporated in vacuo over a period of 30 minutes at a maximum temperature of 27°C. Residual amounts of hydrazine are removed by slurrying the residue with 2 × 5 ml. methanol and by triturating with 3 × 10 ml. ethyl ether and decanting. A Tollens test indicates the solid residue is free of hydrazine. The solid is triturated with 2 × 3 ml. cold water and filtered to remove a contaminant observed on tlc plates at R$_f$ O in the solvent system 70:30:3 (chloroform:methanol:water). The dry hydrazide, weighing 214 mg., chromatographs essentially as one spot on tlc plates in the system 70:30:3 (chloroform:methanol:water using Sanger, tert-butylhypochlorite-KI, Ehrlich and Tollens sprays for identification.

EXAMPLE 25

Preparation of Pyroglu-His-Trp-Ser-Tyr Azide

A solution of 214 mg. (0.3 mmole) of pyroglu-his-trp-ser-tyr-NHNH$_2$ in 2 ml. of dry, degassed DMF is cooled to −40°C. and the flask flushed with dry nitrogen. A solution of 0.60 ml. (1.20 mmoles, 4 eq.) of dry 2N HCl in THF is added to make the solution pH 1 – 2. While holding the temperature at −40°C. in an alcohol dry ice bath, 40 $\mu$-l. of isoamyl nitrite is added to the stirred solution in six small portions over a period of 2 hours. The pH 1 is maintained by addition of 0.6 ml. 2N HCl in THF. With each addition of nitrite, the disappearance of the hydrazide is tested with Tollens reagent and the presence of an excess of nitrite is demonstrated with iodide-starch test paper.

EXAMPLE 26

Preparation of tBOC-Gly-Resin

Forty grams (76 mmole) of chloromethylresin having 1.90 meq. chlorine/g., and 13.3 g. (76 mmole; 1 equivalent) of tBOC-gly is added to 250 ml. of peroxide-free tetrahydrofuran. The mixture is stirred in an oil bath at 76°C. for 45 minutes. Triethylamine (10 ml.) is added, the reaction is stirred at 76°C. for 77 hours, cooled to 25°C. and transferred to a Merrifield solid phase rocking reaction vessel. After removal of the solvent, the resin is washed, using the shaker, with the following solvents:

3 × 100 ml. of THF
4 × 250 ml. of ethanol
1 × 250 ml. of acetic acid
3 × 250 ml. of water
3 × 250 ml. of methanol
3 × 250 ml. of methylene chloride
3 × 250 ml. of chloroform The tBOC-gly-resin is dried in vacuo at 25°C. for 16 hours, giving 45.7 g. of tBOC-gly-resin containing 0.781 $\mu$mole of gly/mg. of resin.

EXAMPLE 27

Preparation of tBOC-Gly-Leu-Arg(NO$_2$)-Pro-Gly-Resin

The tBOC-gly-resin (20 g.; 15.6 mmole) while in the Merrifield solid phase rocking reaction vessel is repeatedly carried through the series of steps shown below using 250 ml. of solvents, two deblockings (5 minutes + 30 minutes) with HCl-dioxane, and 2.5 equivalents of the following tBOC-aminoacid in each cycle:

| | |
|---|---|
| tBOC-Proline | 8.4 g. |
| tBOC-Nitroarginine | 12.5 g. |
| tBOC-Leucine.H$_2$O | 9.7 g. |
| tBOC-Glycine | 6.8 g. |

3 × 250 ml. dioxane, 3 minutes, filter
1 × 250 ml. 4N HCl in dioxane, 5 minutes, filter
1 × 250 ml. 4N HCl in dioxane, 30 minutes, filter
3 × 250 ml. dioxane, 3 minutes, filter
3 × 250 ml. chloroform, 3 minutes, filter
1 × 250 ml. triethylamine-chloroform (1:9), 10 minutes, filter
3 × 250 ml. chloroform, 3 minutes, filter
3 × 250 ml. methylene chloride, 3 minutes, filter
tBOC-amino acid in a minumum amount of methylene chloride (75 ml.) and in the case of tBOC-nitroarginine 17 ml. of dimethylformamide and in the case of tBOC-leucine.H$_2$O 7 ml. of dimethylformamide, shake 5 minutes, do not filter
DCC in 16.1 ml. methylene chloride containing 0.5 gm. DCC/ml. methylene chloride, 4 hours, filter
3 × 250 ml. methylene chloride, 3 minutes, filter.
2 × 250 ml. DMF
2 × 250 ml. methylene chloride.

The tBOC-pentapeptide-resin is washed with:
3 × 250 ml. ethanol
3 × 150 ml. acetic acid
5 × ml. ethanol
3 × 250 ml. methylene chloride After the product has been dried in vacuo for several days it weighs 26.7 g. By weight gain, it contains 0.581 mmole of peptide/g. By amino acid analysis it contains 0.38 mmole of peptide/g.

Amino acid analysis after acid hydrolysis gives the following results:

| | $\mu$mol./mg. | Normalized |
|---|---|---|
| NH$_3$ | .199 | .49 |
| Arg (1) | .254 | .63 |
| Pro (1) | .388 | .96 |
| Gly·(2) | .801 | 1.99 |
| Leu (1) | .423 | 1.05 |
| NO$_2$Arg | .063 | .16 |
| Orn | .062 | .15 |

EXAMPLE 28

Preparation of Gly-Leu-Arg-Pro-Gly-OH.2HOAc

A sample of 5.4 g. of tBOC-gly-leu-arg-(NO$_2$)-pro-gly-resin in 25 ml. of liquid HF is stirred at 0°C. for 30 minutes. After evaporating the HF at 0°C. with a stream of dry nitrogen and also in vacuum, the residue is placed in a sintered glass funnel and leached with several portions of ethyl acetate to remove traces to HF. The pentapeptide is extracted by slurrying with 10 × 30 ml. of 1% aqueous acetic acid until the last extract gives a negative test with tert-butylhypochlorite-KI and starch and with ninhydrin. The combined extracts are freeze-dried to yield 1.21 g. of white solid which is essentially pure by tlc in the systems: 65:10:25 (butanol:acetic acid:water), 60:30:4:6 (chloroform: methanol:water:ammonia) and 60:40:10 (chloroform:methanol:water) using tert-butylhypochlorite-KI spray for identification.

EXAMPLE 29

Preparation of Pyroglu-His-Trp-Ser-Tyr-Gly-Leu-Arg-Pro-Gly-OH (LH-RH-[1-9]-10-Glycine-OH)

To the pentapeptide azide solution in situ, prepared as described in Example 25, is added 196 mg. (0.315 mmoles, a 5% excess) of dry, powdered gly-leu-arg-pro-gly-OH.2HOAc, 0.22 ml. (0.4 mmoles, 5 eq.) of triethylamine to adjust the solution to pH 7.5 and 0.5 ml. of DMF. The slurry is stirred at −10°C. for 30 minutes and at +4°C. for 16 hours. The decapeptide is precipitated by adding the reaction mixture to a stirred solution of 30 ml. of ethyl ether and 40 ml. petroleum ether at 0°C. The supernatant is decanted from the yellow oil that separates. The oil is washed further by slurrying at 0°C. with 60 ml. ethyl ether and with 30 ml. of ethyl ether containing 3 ml. methanol. The oil is dried to a yellow solid decapeptide weighing 475 mg. This decapeptide is found by tlc developed in the 60:40:10 (chloroform:methanol:water) system and sprayed with tert-butylhypochlorite-KI and starch and with phenanthraquinone arginine reagents to contain a small amount of the arginine pentapeptide.

EXAMPLE 30

Chromatographic Purification of LH-RH-[1-9]-10-Glycine-OH a. Sephadex G-25

The arginine containing pentapeptide is separated from the decapeptide in a column packed with Sephadex superfine G-25 molecular sieve and developed with 50% acetic acid. The combined rich cuts (28 – 35, 72 ml.) of the decapeptide are concentrated in vacuum and freeze-dried to yield 269 mg. of solid. Tlc plates developed in the solvent systems 50:40:4:6 (chloroform:methanol:water:acetic acid) and 60:40:10 (chloroform:methanol:water) indicates that some arginine pentapeptide is still contaminating the decapeptide. The following amino acid analysis confirms this:

| Amino Acid | Micromoles/mg. |
|---|---|
| Glutamic Acid | 0.664 |
| Histidine | 0.620 |
| Trytophane | 0.360 |
| Serine | 0.654 |
| Tyrosine | 0.632 |
| Glycine | 1.459 |
| Leucine | 0.759 |
| Arginine | 0.680 |
| Proline | 0.750 | b. Silica Gel Dry Column

A solution of 228 mg. of the above decapeptide in a few ml. of 60:40:10 (chloroform:methanol:water) is applied on a silica gel dry column. The chromatogram is developed with 60:40:10 solvent. The rich cuts, found by tlc in solvent system 60:40:10 to be single spot decapeptide, are segregated into two groups. Fractions 45–52 (64 ml.) are concentrated in vacuum and freeze-dried to yield 110 mg. of white solid. Fractions 53–61 (72 ml.) are similarly treated to yield 101 mg. of white solid. The amino acid analyses of these two decapeptide samples follows:

| Amino Acid | Micromoles/mg. fractions 45–52 | fractions 53–61 |
|---|---|---|
| Glutamic Acid | 0.678 | 0.728 |
| Histidine | 0.597 | 0.634 |
| Tryptophane | 0.569 | 0.623 |
| Serine | 0.677 | 0.741 |
| Tyrosine | 0.580 | 0.765 |
| Glycine | 1.321 | 1.410 |
| Leucine | 0.697 | 0.708 |
| Arginine | 0.653 | 0.685 |
| Proline | 0.649 | 0.753 |

EXAMPLE 31

Preparation of LH-RH-[1-9]-10-Glycyl-Poly-L-Lysine a. Formation of the "Active Ester" with 1-Hydroxybenztriazole:

A solution of the peptide, "LH-RH acid" (pyro-glu-his-trp-ser-tyr-glu-leu-arg-pro-gly-OH, having a free carboxyl on the C-terminal glycine residue) "active ester" is made by combining 25 mg. of this peptide (M. W. 997, 0.025 mmole) with a three-fold excess, 11 mg., of 1-hydroxybenztriazole (M. W. 135, 0.075 mmole) in 0.75 ml. of dry dimethylformamide which had been redistilled prior to use to remove interfering amines. The mixture is stirred under dry nitrogen, cooled in an ice bath, and a slight excess, 0.12 ml., of a solution of dicyclohexylcarbodiimide (DDC) in dry dichloromethane (0.242 mmole of DDC/ml. of $CH_2Cl_2$-total added 0.029 mmole) is added. After 2 hours in the ice bath, the mixture is left stirring overnight at room temperature under dry nitrogen.

The active ester of LH-RH acid (C-terminal-1-hydroxybenztriazolyglycine ester) is prepared for coupling with poly-L-lysine by concentrating to dryness under a stream of dry $N_2$ and then vigorously extracting three times by trituration with portions of dry methylene chloride, totaling 2 ml. This is done to remove all excess DCC, to prevent polymerization of the medium molecular weight polylysine to an intractable felt-like mass in the coupling step. The residue is dissolved in 0.25 ml. of dry, pure dimethylformamide for coupling to poly-L-lysine in the next step.

b. Coupling to Poly-L-Lysine

A mixture is made of 50 mg. of poly-L-lysine hydrochloride, 0.5 ml. of dry DMF and 0.15 ml. of water. After adjusting the pH of the solution to 8 with 5N alkali, the poly-L-lysine is essentially all in solution except for a trace of opalescence. The LH-RH peptide-active ester solution in 0.25 ml. of dimethylformamide, prepared as illustrated in Step A above, is added and mixed. The pH is adjusted to 9.5 with another trace of aqueous 5N alkali, and the mixture is stirred under $N_2$ overnight. After stirring overnight the pH is raised to 10 with triethylamine, and stirring under nitrogen at room temperature is again continued overnight. Samples chromatographed on thin layer silica gel plates in chloroform-methanol-water, 50:40:10, shows covalently-linked material at the origin, and unreacted LH-RH peptide at $R_f$ 0.65 – 0.75, when sprayed with Ehrlich's spray for tryptophan residues.

About one volume of water is added to the reaction; it is then acidified with hydrochloric acid until a pH of 2.5 is reached and then concentrated to dryness under vacuum. The residue is extracted three times with methanol diluted with ether. Samples of the remaining residue chromatographed by thin layer chromatography show that unreacted LH-RH peptide has been removed and the insoluble poly-L-lysine-like material remaining at the origin has a strong Ehrlich reaction indicating presence of tryptophan. The residue is taken up in water, filtered and lyophilized to constant weight to yield 43.2 mg. of the antigen, pyroglutamyl-histidyl-tryptophanyl-seryl-tyrosyl-glycyl-leucyl-arginyl-prolyl-glycyl-$N^\epsilon$-poly-L-lysine hydrochloride.

Amino acid analysis of a 0.60 mg. sample shows a molar ratio of His, 1.13; Arg, 0.96; Ser, 0.86; Glu, 1.01; Pro, 1.02; Gly 2.0; Leu, 1.03; and Tyr, 1.0 (tryptophan not reported, lysine too high to read). The degree of coupling determined on the basis of glycine content (0.246 mmol/mg) is 20% by weight.

EXAMPLE 32

Preparation of Poly-L-Lysine Hydrochloride

To a suspension of 10.72 g. of $N^\epsilon$-Cbz-L-lysine NCA (35 mmole) in 100 ml. of dry dimethylformamide (previously fractionated over $P_2O_5$) is added 398 mg. of sodium methoxide (7 mmole) and the mixture allowed to stand at room temperature for two days. Two ml. of 50% acetic acid is then added and the solvent removed under vacuum. The residue is treated with 2 ml. of veratrole (o-dimethoxybenzene) and 25 ml. of anhydrous HF at 0°C. for 1 hour to deblock the lysine residues. The HF is then evaporated in a stream of nitrogen and the residue triturated with ether, leaving 6.6 g. of residual solid. This is dissolved in 35 ml. of 0.02 M ammonium acetate buffer, the pH is adjusted to 6 with ammonium hydroxide, and 4 ml. of chloroform is added. The two layers are mixed and the mixture centrifuged at 13,000 r.p.m. for 30 minutes to separate the chloroform layer containing veratrole. The supernatant acetate buffer layer containing the product is fractionated on a 5 × 110 cm. column of Sephadex G-100 molecular sieve in 0.02 M ammonium acetate buffer. Collection of cuts of 13.5 ml. yields a zone in cuts numbers 66–86 representing an average molecular weight of 40,000–80,000. These are combined, lyophilized, and the residue is then passed over a 500 ml. Dowex 1 × 8 column on acetate cycle to remove fluoride ions. The effluent is lyophilized, redissolved and passed over a 350 ml. Dowex 1 × 8 column on the chloride cycle, to convert the product to the chloride salt; the effluent is lyophilized to yield 325 mg. white residue. Amino acid analysis indicated 86% lysine by weight.

The antigens of this invention are useful for controlling the menstrual cycle and ovulation in animals. Specifically, these antigens are useful, for example in the veterinary field as an alternative to spaying of canine and feline pets. These synthetic antigens are conveniently administered by injection. An effective amount of the antigen is ordinarily supplied at a dosage level of from about 0.1 mg. to about 50 mg./kg. of body weight. Preferably the range is from about 0.1 mg. to 10 mg./kg. body weight each 5 to 7 months period but preferably every 6 months period. For example in a household pet such as a cat or dog, 1 mg./kg. body weight administered every 6 months period in order to maintain its ability to avoid conception.

The following examples are included to illustrate the preparation of a representative doses of antigen.

EXAMPLE 33

Injectable Solution of
LH-RH-[1-9]-10-Glycyl-Poly-L-Lysine

LH-RH-[1-9]-10-glycyl-poly-L-lysine is dissolved in isotonic saline and adjusted to pH 6.5 with phosphate buffer to make a solution containing 6 mg./ml. Equal volumes of this solution and complete adjuvant are emulsified and injected subcutaneously or intradermally or preferably intramuscularly at a dosage of 1 mg./kg. of body weight.

EXAMPLE 34

Injectable Solution of
1-$N^\alpha$-Glutaryl-LH-RH-[2-10]-Poly-L-Lysine

1-$N^\alpha$-glutaryl-LH-RH-[2-10]-poly-L-lysine is dissolved in isotonic saline and adjusted to pH 6.5 with phosphate buffer to make a solution containing 6 mg./ml. Equal volumes of this solution and complete adjuvant are emulsified and injected subcutaneously or intradermally or preferably intramuscularly at a dosage of 1 mg./kg. of body weight.

What is claimed is:

1. The antigen 1-$N^\alpha$-glutaryl-LH-RH-[2-10]-carrier wherein the peptide 1-$N^\alpha$-glutaryl-LH-RH-[2-10], having the amino acid sequence glutaryl-his-trp-ser-tyr-gly-leu-arg-pro-gly-$NH_2$, is linked to a carrier selected from the group consisting of $\alpha$, $\beta$ and $\gamma$ globulins, thyroglobulins, Keyhole Limpet Hemocyanin, poly-L-glutamic acid, and poly-L-lysine by a peptide linkage between the carboxyl group of the glutaryl moiety and the amino groups of said carrier.

2. The antigen 1-$N^\alpha$-glutaryl-LH-RH-[2-10]-carrier wherein the peptide 1-$N^\alpha$-glutaryl-LH-RH-[2-10] is linked to poly-L-lysine carrier by a peptide linkage between the carboxyl group of the glutaryl moiety and the $\epsilon$-amino groups of lysyl residues in poly-L-lysine.

3. The antigen according to claim 2 wherein the average molecular weight of the poly-L-lysine carrier is between 40,000 and 80,000.

4. The peptide having the structure: glutaryl-his-trp-ser-tyr-gly-leu-arg-pro-gly-$NH_2$.

5. The process for preparing the antigen 1-$N^\alpha$-glutaryl-LH-RH-[2-10]-carrier which comprises:
   a. reacting the methyl or ethyl ester of histidine with glutaric anhydride to form the dipeptide $N^\alpha$-glutaryl-his-OMe or $N^\alpha$-glutaryl-his-OEt;
   b. reacting said dipeptide, $N^\alpha$-glutaryl-his-OMe or $N^\alpha$-glutaryl-his-OEt, with hydrazine to form the corresponding hydrazide, $N^\alpha$-glutaryl-his-$NHNH_2$;
   c. reacting said hydrazide, $N^\alpha$-glutaryl-his-$NHNH_2$, with isoamyl nitrite to form the azide, $N^\alpha$-glutaryl-his-$N_3$;
   d. reacting said azide, $N^\alpha$-glutaryl-his-$N_3$, with the methyl or ethyl ester of trp-ser-tyr to form the corresponding pentapeptide $N^\alpha$-glutaryl-his-trp-ser-tyr-OMe or $N^\alpha$-glutaryl-his-trp-ser-tyr-OEt;
   e. reacting said pentapeptide, $N^\alpha$-glutaryl-his-trp-ser-tyr-OMe or $N^\alpha$-glutaryl-his-trp-ser-tyr-OEt, with hydrazine and isoamyl nitrite as in step b) and c) to form the azide, $N^\alpha$-glutaryl-his-trp-ser-tyr-$N_3$;
   f. reacting said azide, $N^\alpha$-glutaryl-his-trp-ser-tyr-$N_3$, with the pentapeptide, gly-leu-arg-pro-gly-$NH_2$, thereby forming the decapeptide having the amino acid sequence, glutaryl-his-trp-ser-tyr-gly-leu-arg-pro-gly-$NH_2$ and linking said decapeptide by a peptide linkage between the carboxyl group of the glutaryl moiety of the decapeptide and the amino groups of a carrier selected from the group consisting of $\alpha$, $\beta$ and $\gamma$ globulins, thyroglobulins, Keyhole Limpet Hemocyanin, poly-L-glutamic acid and poly-L-lysine.

6. The process according to claim 5 for preparing the antigen, 1-$N^\alpha$-glutaryl-LH-RH-[2-10]-poly-L-lysine, which comprises steps (a) to (f) to form the decapeptide having the amino acid sequence, glutaryl-his-trp-ser-tyr-gly-leu-arg-pro-gly-$NH_2$, and linking said decapeptide by a peptide linkage between the carboxyl group of the glutaryl moiety and the $\epsilon$-amino groups of lysyl residues in poly-L-lysine.

7. The process according to claim 6 wherein the process comprises forming the active ester of the peptide having the amino acid sequence glutaryl-his-trp-ser-tyr-gly-leu-arg-pro-gly-$NH_2$ with [1-hydroxybenzotriazole] and reacting said active ester with the $\epsilon$-amino groups of lysyl residues in poly-L-lysine.

* * * * *